United States Patent
Budai et al.

[11] 4,342,762
[45] Aug. 3, 1982

[54] BASIC ETHERS AND PHARMACEUTICAL COMPOSITIONS CONTAINING THE SAME

[75] Inventors: Zoltan Budai; Laszlo Magdanyi; Aranka Lay nee Konya; Tibor Mezei; Katalin Grasser; Lujza Petöcz; Ibolya Kosoczky, all of Budapest, Hungary

[73] Assignee: Egyt Gyogyszervegyeszeti Gyar, Budapest, Hungary

[21] Appl. No.: 215,154

[22] Filed: Dec. 11, 1980

[30] Foreign Application Priority Data

Dec. 14, 1979 [HU] Hungary .............................. EE 2715

[51] Int. Cl.³ .................. A61K 31/54; A61K 31/495; A61K 31/445; C07D 245/02
[52] U.S. Cl. ............................... 424/246; 424/248.51; 424/248.57; 424/250; 424/267; 424/274; 424/275; 424/330; 260/239 B; 260/330.3; 544/59; 544/60; 544/146; 544/174; 544/379; 544/394; 544/392; 544/398; 549/75; 564/428; 564/454; 548/576
[58] Field of Search ....................... 564/453, 428, 454; 260/239 B, 326.5 R, 326.5 SM, 326.5 C; 219/82; 546/205, 206; 549/75; 424/248.56, 325, 246, 248.57, 250, 267, 274, 275, 330, 248.51; 544/59, 173, 392, 398, 60, 158, 374, 146, 174, 379, 394

[56] References Cited

U.S. PATENT DOCUMENTS 4,118,499 10/1978 Stephenson et al. ................. 564/453
4,294,829 10/1981 Suzuki et al. ........................ 424/330

Primary Examiner—Natalie Trousof
Assistant Examiner—Frederick W. Pepper
Attorney, Agent, or Firm—Karl F. Ross

[57] ABSTRACT

The invention relates to novel basic ethers of the general formula /I/ and pharmaceutically acceptable acid addition salts and quaternary salts thereof,

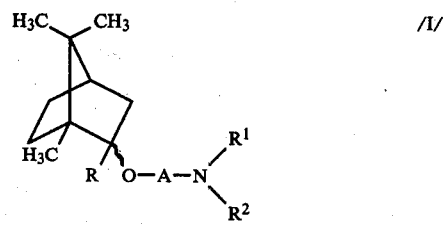

wherein
  $R^1$ and $R^2$ may be the same or different and represent a $C_{1-5}$ alkyl group or a $C_{3-6}$ cycloalkyl group or they form, together with the adjacent nitrogen atom, a heterocyclic ring containing 4–7 carbon atoms and optionally a further hetero atom, e.g. an oxygen, sulfur or nitrogen atom, and this latter may be optionally substituted by a $C_{1-3}$ alkyl, benzyl or phenyl group,
  R represents a phenyl, phenyl-/$C_{1-3}$ alkyl/ or thienyl group optionally substituted by one or more halogen or $C_{1-3}$ alkoxy substituent/s/,
  A represents a $C_{2-5}$ straight or branched alkylene chain, and ⁓ represents a valence bond of $\alpha$ or $\beta$ configuration.

The new compounds of the general formula /I/ possess valuable anticonvulsive, motility inhibiting, hexobarbital narcose potentiating and analgesic effects, which are, in case of certain compounds, complemented by week antiserotonine, gastro-intestinal-tract inhibiting and antiinflammatory effects, and can be applied to advantage in the therapy.

8 Claims, No Drawings

BASIC ETHERS AND PHARMACEUTICAL COMPOSITIONS CONTAINING THE SAME

This invention relates to novel basic ethers of valuable therapeutic effect and to a process for their preparation. The invention relates also to pharmaceutical compositions containing the said compounds.

The present invention provides compounds of the formula (I)

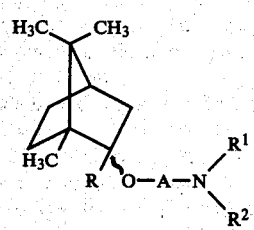

and pharmaceutically acceptable acid addition salts and quaternary salts, thereof.

In this formula:

$R^1$ and $R^2$ are the same or different and can be a $C_{1-5}$ alkyl group or a $C_{3-6}$ cycloalkyl group or they form, together with the adjacent nitrogen atom, a heterocyclic ring containing 4–7 carbon atoms and optionally a further hetero atom, e.g. an oxygen, sulfur or nitrogen atom, and this latter may be optionally substituted by a $C_{1-3}$ alkyl, benzyl or phenyl group, R represents a phenyl, phenyl-($C_{1-3}$ alkyl) or thienyl group optionally substituted by one or more halogen or $C_{1-3}$ alkoxy substituents, A represents a $C_{2-5}$ straight or branched alkylene chain, and represents a valence bond of $\alpha$ or $\beta$ configuration.

The invention also embraces all steric isomers of the compounds of the formula (I) and the mixtures thereof.

The compounds of the formula (I) contain, depending on the definition of the substituents, two or more centers of asymmetry, consequently they exist in the form of one or more racemic mixtures or two or more optically active antipodes. The invention embraces the racemic and optically active forms of the compounds of the formula (I), too.

The term "$C_{1-5}$ alkyl group" relates to straight or branched saturated aliphatic hydrocarbyl groups, such as methyl, ethyl, n-propyl, isopropyl, n-butyl, isobutyl, etc. The term "$C_{3-6}$ cycloalkyl group" may be cyclopropyl, cyclobutyl, cyclopentyl or cyclohexyl group. The heterocyclic ring formed by $R^1$, $R^2$ and the adjacent nitrogen atom may be piperidine, pyrrolidine, morpholine, thiomorpholine, piperazine, N-methyl-piperazine, N-phenyl-piperazine or N-benzyl-piperazine, etc.

The term "phenyl-($C_{1-3}$ alkyl) group" can mean a benzyl or β-phenylethyl group. The term "$C_{1-3}$ alkoxy group" relates to straight or branched lower alkylether groups, such as methoxy, ethoxy, n-propoxy, isopropoxy, etc. The term "halogen atom" may stand for all the four halogen atoms, fluorine, chlorine, iodine, bromine. The term "$C_{2-5}$ alkenyl group" refers to straight or branched lower alkenyl groups, such as ethylene, propylene, 2-methyl-propylene, butylene, 2-methyl-butylene, etc.

Preferred representatives of the new compounds having the formula (I) are those wherein:

$R^1$ and $R^2$ each represent methyl or ethyl group,

R denotes phenyl, benzyl or $C_{1-3}$-alkoxy-phenyl group, and

A denotes ethylene, propylene or 2-methyl-propylene group.

Of the new compounds of the formula (I) the following are particularly preferred:

2-benzyl-2-(3'-dimethylamino-2'-methyl-propoxy)-1,7,7-trimethyl-bicyclo(2,2,1)heptane, 2-benzyl-2-(3'-diethylaminopropoxy)-1,7,7-trimethyl-bicyclo(2,2,1)heptane, 2-benzyl-2-(2'-diethylaminoethoxy)-1,7,7-trimethyl-bicyclo(2,2,1)heptane, and the pharmaceutically acceptable acid addition salts of these compounds.

The following compounds of the formula (I) have the most valuable pharmaceutical activities:

2-phenyl-2-(3'-dimethylaminopropoxy)-1,7,7-trimethyl-bicyclo(2,2,1)heptane, 2-phenyl-2-(2'-dimethylaminoethoxy)-1,7,7-trimethyl-bicyclo(2,2,1) heptane, 2-phenyl-2-(3'-diethylaminopropoxy)-1,7,7-trimethyl-bicyclo-)(2,2,1) heptane, 2-(p-methoxy-phenyl)-2-(3'-dimethylaminopropoxy)-1,7,7-trimethyl-bicyclo(2,2,1) heptane, and pharmaceutically acceptable acid addition salts of these compounds.

The pharmaceutically acceptable acid addition salts of the compounds of the formula (I) can be formed with inorganic or organic acids generally used for this purpose, e.g. with hydrogen chloride, hydrogen bromide, sulfuric, phosphoric, acetic, lactic, propionic, methanesulfonic, tartaric, maleic, fumaric acids, etc. The quaternary salts of the compounds of the formula (I) can be formed with reactants usually applied for quaternarization, e.g. with lower alkyl halogenides, such as methyl iodide or methyl chloride, dialkyl-sulfates, such as diethylsufate, n-propyl iodide, etc.

According to a further feature of the present invention there is provided a process for the preparation of basic ethers of the formula (I) and pharmaceutically acceptable acid addition salts and quaternary salts thereof, which comprises:

a. reacting a compound of the formula (II)

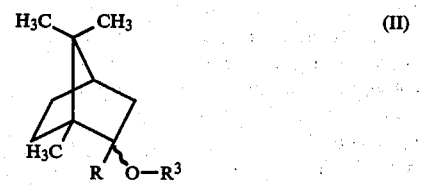

wherein

R has the same meaning as above, whereas $R^3$ denotes an alkali metal atom, an alkali-earth metal atom or a group of the general formula X-Me, wherein X denotes halogen and Me stands for alkali-earth metal atom, with a compound of the formula (III)

wherein Y stands for halogen and A, $R^1$ and $R^2$ have the same meaning as above; or b. treating a compound of the formula (IV)

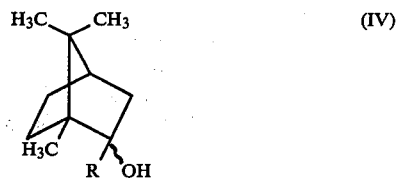

wherein R has the same meaning as above, with an agent suitable to introduce an $R^3$ group and reacting the compound of the formula (II) thus-obtained, wherein R and $R^3$ have the above-defined meanings, with a compound of the formula (III); or c. reacting 1,7,7-trimethyl-bicyclo(2,2,1)heptane-2-one with an organo-metallic compound, decomposing the complex thus-obtained, and reacting the compound of the formula (IV) thus obtained, wherein R has the above defined meaning, with a base suitable to introduce an $R^3$ group, and reacting the compound of the formula (II) thus obtained with a compound of the formula (III), and, if desired, converting the compound of the formula (I) thus obtained into a pharmaceutically acceptable acid addition salt or quaternary salt.

The reaction of the compounds of the formulae (II) and (III) can be carried out in an organic solvent, such as benzene, toluene, xylene, dimethylacetamide, dimethylsulfoxide, dimethylformamide, tetrahydrofurane or a mixture thereof. The reaction can be performed in a wide temperature range, e.g. from $-10°$ C. to $200°$ C., preferably at a temperature between $10°$ C. and $100°$ C.

The compounds of the formula (I) can be isolated from the reaction mixture by methods known per se, e.g. evaporating the reaction mixture, extracting with a suitable organic solvent, etc.

The compounds of the formula (II) can be prepared by reacting a compound of the formula (IV) with a reactant suitable to introduce an $R^3$ group. Alkali metals (e.g. lithium, sodium or potassium) and hydrides or amides of the respective metals (e.g. sodium hydride, potassium hydride, sodium amide, potassium amide,) are preferably used for this purpose.

The compounds of the formula (IV) can be produced by reacting 1,7,7-trimethyl-bicyclo(2,2,1) heptane-2-one of the formula (V) with an organo-metallic compound and decomposing the complex thus-obtained. As organo-metallic compounds sodium- or lithium-compounds or Grignard-reagents can be applied. The organo-metallic compound contains an organic radical corresponding to the $R^3$ group. The reaction can be performed in an inert solvent in a known matter. As the reaction medium, diethylether, tetrahydrofurane, diisopropylether, benzene, petrolether, etc. can be used. The reaction temperature can range over a wide interval. The reaction can preferably carried out between $10°$ C. and $100°$ C.

According to a preferred method of the invention the starting compound of the formula (II) prepared by reacting a compound of the formula (IV) with a reagent suitable to introduce an $R^3$ group is not isolated, but the compound of the formula (III) is added to the reaction mixture containing the compound of the formula (II).

The compound of the formula (V) is a commercial product. The starting compounds of the formula (III) are known products.

The acid addition salts and quaternary salts of the compounds of the formula (I) can be prepared by methods known per se. To prepare an acid addition salt a base of the formula (I) is reacted with optionally one mole-equivalent amount of the respective acid. To prepare a quaternary salt a base of the formula (I) is reacted with optionally one mole-equivalent amount of the respective quaternarizing agent in an organic solvent.

The optically active antipodes of the formula (I) can be prepared by using optically active starting compounds or by resolving the respective racemic compound by a method known per se. For this purpose a racemic compound of the formula (I) is reacted with an optically active acid, such as tartaric acid, O,O-dibenzoyl-tartaric acid, O,O-di-p-toluene-tartaric acid or camphor-sulfonic acid, the diastereomeric salt-pair thus-obtained is separated by fractionated crystallization, and the optically active isomer is liberated from the salt by reacting it with a base under mild conditions. The fractional crystallization can be carried out in a suitable solvent, e.g. methanol, water, etc.

According to our investigations the compounds of the formula (I) have proved to be biologically active in several tests and possess particularly tranquillizing, anti-Parkinsonism, analgesic and antiepileptic effects. Of these biological effects the most significants were: the anti-convulsive, motility inhibiting, hexobarbital-narcosis potentiating and analgesic effects which are, in case of certain compounds, complemented by week antiserotonine, gastro-intestinal-tract inhibiting and antiinflammatory effects.

The analgesic effect of the new compounds according to the invention was determined by the method of Wirth et al. (Wirth, W., Gösswald, R., Hörlein. K., Risse, Kl. H., Kreiskott, H.: Arch. Int. Pharmacodyn. 115, 1; (1958)). 0.4 ml of 0.5% acetic acid was administered i.p. to white mice, and the characteristic "writhing" reactions were counted after 5 minutes. The compounds to be tested had been orally administered an hour before the administration of the acetic acid. The activity is expressed as a percentage of the inhibition referred to the data observed on the control group. The results are given in Table I. The toxicity data determined on white mice of both sexes weighing 18–24 g belonging to the strain CFLP are also given. Administration was effected with an oral dose of 20 ml/kg. After treatment the animals were kept under observation for 4 days. The toxicity data ($LD_{50}$ mg/kg) were determined by the graphic method of Litchfield-Wilcoxon [Litchfield, J.T., Wilcoxon, E. W., J Pharmacol. Exp. Therap. 96, 99; (1949)].

TABLE I

| Compound No. of Example | $LD_{50}$ mg/kg | Analgesic effect | |
|---|---|---|---|
| | | $ED_{50}$ mg/kg | Therap.index |
| 1 | 1600 | 120 | 13.3 |
| 2 | 1700 | 85 | 20.0 |
| 3 | 1250 | 120 | 10.4 |
| 4 | 2000 | 200 | 10.0 |
| 5 | 2000 | 100 | 20.0 |
| 6 | 2000 | 50 | 40.0 |
| 7 | 1200 | 70 | 17.1 |
| 8 | 850 | 45 | 18.9 |
| 11 | 1500 | 75 | 20.0 |
| 12 | 2000 | 100 | 20.0 |
| 13 | 2000 | 200 | 10.0 |
| 14 | 1000 | 50 | 20.0 |

TABLE I-continued

| Compound No. of Example | LD$_{50}$ mg/kg | Analgesic effect | |
|---|---|---|---|
| | | ED$_{50}$ mg/kg | Therap.index |
| 15 | 900 | 23 | 39.0 |
| 16 | 700 | 70 | 10.0 |
| 17 | 980 | 50 | 19.6 |
| 18 | 1400 | 140 | 10.0 |
| 19 | 1000 | 120 | 8.3 |
| 22 | 1000 | 72 | 13.8 |
| Paracetamole [N-(4-Hydroxyphenyl)-acetamide] | 510 | 180 | 2.8 |

Therapeutic index = $\dfrac{LD_{50}}{ED_{50}}$

The antiepileptic effect was investigated on white mice, after oral administration. The inhibition of maximal electroshock (MES) was determined by the method of Swinyard et al. [Swinyard et al. J. Pharmacol. Exp. Ther. 106, 319–330 (1952)]. White mice weighing 20–25 g were subjected to electric shock through corneal electrodes (Parameters: 50 Hz, 45 mA, 0.4 sec.). The total inhibition of the tonic extensor convulsion was considered as criterion of the anti-convulsive effect. The test-substance had been orally administered one hour before the electroshock. The inhibition of pentetrazole convulsion was determined on white mice by the modified method of Banziger and Hane [Banziger, R., Hane, L.D. Arch. Int. Pharmacodyn. 167, 245–249; (1967)]. The results are given in Table II, wherein "Th. I." stands for "therapeutic index."

TABLE II

| Compound No. of Example | MES | | Inhibition of pentetrazole convulsion | |
|---|---|---|---|---|
| | ED$_{50}$ mg/kg | Th. I. | ED$_{50}$ mg/kg | Th. I. |
| 1 | 130 | 12.3 | — | — |
| 2 | 120 | 14.2 | 88 | 19.3 |
| 5 | 380 | 5.3 | 140 | 14.3 |
| 6 | 120 | 16.7 | 54 | 37.0 |
| 7 | 56 | 21.4 | 66 | 18.2 |
| 8 | 30 | 28.3 | 20 | 42.5 |
| 12 | 72 | 27.7 | 110 | 18.2 |
| 13 | 140 | 14.3 | 140 | 14.3 |
| 16 | 30 | 23.3 | 60 | 11.7 |
| 17 | — | — | 60 | 16.3 |
| 22 | — | — | 96 | 10.4 |
| Trimethadion (3,5,5-Trimethyl-2,4-oxazolidinedione) /Ptimal/ | 4.90 | 4.3 | 400 | 5.3 |

The inhibition of nicotine-lethality was determined on white mice by the method of Stone [Stone, C. A., Mecklenburg, K. L., Torchiana, M. L., Arch. Int. Pharmacodyn. 117, 419; (1958)]. One hour after the oral administration of the test-substance 1.4 mg/kg nicotine were injected and the number of the animals which suffered from convulsions or died was registered. The results are given in Table III.

TABLE III

| Compound No. of Example | ED$_{50}$ mg/kg | Therapeutic index |
|---|---|---|
| 1 | 38 | 42.1 |
| 2 | 20 | 85,0 |
| 7 | 25 | 48.0 |
| 8 | 11 | 77.3 |
| 15 | 30 | 30.0 |
| 17 | 50 | 19.6 |
| Trihexyphenidyl (α-Cyclohexyl-α-phenyl-1-piperidine-propanol) (Artane) | 40 | 9.13 |

The effect on the inhibition of the oriental activity (inhibition of the motility) was investigated on white mice in a Dews apparatus applied with 8 canals by the method of Borsy [Borsy, J., Csanyi, E., Lazar, I., Arc. Int. Pharmacodyn. 124, 1-2 (1960)]. After an oral pre-treatment of 30 minutes the number of light-interruptions due to the movements of groups consisting of 3-3 mice was registered. The observation lasted for 30 minutes. The effect of the compounds exerted on the duration of hexobarbital-narcosis was tested by the method of Kaergaard [Kaergaard, N. C., Magnussen, M. P., Kampmann, E., Frey, H. H., Arc. Int. Pharmacodyn. 2, 170; (1967)]. Groups of animals consisting of 6-6 mice were treated. 20 ml/kg of 0.9% sodium chloride solution were administered to the animals of the control group, then 40 mg/kg of hexobarbital were injected, i.v. Those animals of the treated group were considered to be of a positive reaction which showed a sleeping period being at least 2.5 times longer then the sleeping period of the control group. The results are given in Table IV.

TABLE IV

| Compound No. of Example | Inhibition of motility | | Potentiating of narcosis | |
|---|---|---|---|---|
| | ED$_{50}$ mg/kg | Th.I. | ED$_{50}$ mg/kg | Th.I. |
| 1 | 110 | 14.5 | 90 | 17.7 |
| 2 | — | — | 15 | 113.3 |
| 7 | 90 | 13.3 | — | — |
| 3 | — | — | 120 | 10.4 |
| 5 | 190 | 10.5 | 120 | 16.7 |
| 6 | 100 | 20.0 | 80 | 25.0 |
| 8 | 60 | 14.2 | 60 | 14.2 |
| 11 | 130 | 11.5 | 130 | 11.5 |
| 12 | — | — | 200 | 10.0 |
| 13 | 170 | 11.8 | — | — |
| 14 | 38 | 26.3 | 64 | 15.6 |
| 15 | — | — | 40 | 22.5 |
| 16 | — | — | 20 | 35.0 |
| 19 | — | — | 50 | 20.0 |
| 22 | 100 | 10.0 | 80 | 12.5 |
| Meprobamate (2-Methyl-2-propyl-1,3-propanediol) | 270 | 4.1 | 250 | 4.4 |

The compounds of the formula (I) and therapeutically acceptable acid addition salts and quaternary salts thereof can be formulated with the use of additives and/or carriers and/or adjuvants generally used in pharmacy, by standard techniques.

According to a further feature of the present invention there are provided the above pharmaceutical compositions which can be formulated in solid (e.g. tablets, capsules, coated pills, etc.) or liquid (e.g. solution, suspension, or emulsions) form. These pharmaceutical compositions can be administered orally (e.g. as tablets, coated pills, capsules, solutions), rectally (e.g. as suppositories), or parenterally (e.g. as injections).

The carriers may be those generally used in pharmacy (e.g. starch, magnesium stearate, calcium carbonate, polyvinylpyrrolidone, gelatine, lactose, glucose, water). The compositions may also contain suitable additives (e.g. emulsifying, suspending, disintegrating agents, buffers).

The daily oral dose of the compounds of the formula (I) amounts approximately to about 0.25–75 mg. These values are, however, nearly of an informative character and the actually applied dose depends on the circumstances of the given case and the prescription of the physician and may lay below or above the said interval.

The invention is illustrated by the following Examples of non-limiting character:

EXAMPLE 1

Preparation of (±)-2-benzyl-2-(3'-dimethylaminopropoxy)-1,7,7-trimethyl-bicyclo(2,2,1) heptane A suspension of 3.9 g (0.1 mole) of sodium amide in 100 ml of anhydrous benzene is heated to boiling, and a solution of 24.4 g (0.1 mole) of (±)-2-benzyl-1,7,7-trimethyl-bicyclo(2,2,1)-heptan-2-ol in 100 ml of anhydrous benzene is added dropwise, under continuous stirring. When the addition of the above solution is completed the reaction mixture is boiled until the formation of ammonia gas is ceased, and while further continuing the stirring, a solution of 13.4 g (0.11 mole) of 1-dimethylamino-3-chloro-propane in 20 ml of anhydrous benzene is added. After boiling the mixture for further 6 hours it is cooled to 30° C., washed three times with 40 ml of water each, and extracted with a solution of 15 g (0.1 mole) of tartaric acid in 50 ml of water or with 0.11 mole of diluted aqueous hydrochloric acid. The aqueous solution cooled to 0°–5° C. is made alkaline to pH 10 with concentrated ammonium hydroxide. The base separated as an oil is extracted with dichloroethane. On distilling off the solvent, the residue is fractionated in vacuo.

Yield: 30.2 g (92%) of a pale yellow oil
B.p.: 140°–146° C./26.7 Pa

Preparation of the hydrogen fumarate 16.5 g (0.05 mole) of the above base dissolved in 20 ml of acetone are added to a solution of 5.8 g (0.05 mole) of fumaric acid in 60 ml of hot water. On cooling the reaction mixture the separated crystals are filtered off and dried.

Yield: 20.5 g (92%)
M.p.: 103°–104° C.

$$K\left(\frac{octanol}{water}\right) = 6.4 = \text{partition coefficient}$$

Analysis for $C_{26}H_{39}NO_5$ (445.606):
Calculated: C: 70.08%, H: 8.82%, N: 3.14%,
Found: C: 69.04%, H: 9.02%, N: 3.09%.

Preparation of the hydrogen chloride

A solution of 3.3 g (0.01 mole) of the above base in 25 ml of anhydrous ethylacetate is acidified to pH 5 with ethylacetate saturated with hydrochloric acid. The separated crystals are filtered off and dried.

Yield: 3.5 g (95%)
M.p.: 146°–148° C.
Analysis for $C_{22}H_{36}ClNO$ (365.99):
Calculated: C: 79.19%, H: 9.90%, Cl: 9.69 N: 3.83%,
Found: C: 72.01%, H: 9.78%, Cl: 9.67 N: 3.80%.

Preparation of the citrate

A solution of 3.8 g (0.02 mole) of citric acid in 30 ml of ethanol is added to a solution of 6.6 g (0.02 moles) of the above base in 10 ml of acetone. The separated salt is filtered off and dried.

Yield: 9.59 g (89%)
M.p.: 131°–133° C.
Analysis for $C_{28}H_{45}NO_2$ (539.68):
Calculated: C: 62.31%, H: 8.40%, N: 2.60%,
Found: C: 62.13%, H: 8.27%, N: 2.68%.

Preparation of the tartarate

A solution of 3.0 g (0.02 moles) of tartaric acid in 30 ml of ethanol is added to a solution of 6.6 g (0.02 moles) of the above base in 10 ml of acetone. The separated salt is filtered off and dried.

Yield: 8.82 g (92%)
M.p.: 92°–94° C.
Analysis for $C_{26}H_{41}NO_7$ (479.62):
Calculated: C: 65.11%, H: 8.62%, N: 2.92%,
Found: C: 65.37%, H: 8.73%, N: 2.87%.

Preparation of the iodomethylate

A solution of 2.82 g (0.02 mole) of methyl iodide in 50 ml of acetone is added to a solution of 6.6 g (0.02 mole) of the above base in 50 ml of acetone, then the reaction mixture is allowed to stand at room-temperature for a night. The separated salt is filtered off and dried.

Yield: 8.3 g (88%)
M.p.: 187°–189° C. (decomp.)
Analysis for $C_{23}H_{38}INO$ (471.48):
Calculated: C: 58.59%, H: 8.12%, I: 26.92%, N: 2.97%,
Found: C: 58.68%, H: 8.24%, I: 27.05%, N: 2.93%.

EXAMPLE 2

Preparation of (±)-2-benzyl-2-(3'-dimethylamino-2'-methylpropoxy)-1,7,7-trimethyl-bicyclo(2,2,1) heptane A solution of 24.4 g (0.1 mole) of (±)-2-benzyl-1,7,7-trimethyl-bicyclo(2,2,1) heptan-2-ol in 100 ml of anhydrous toluene is added dropwise, under stirring, to a suspension of 2.4 g (0.1 mole) of sodium hydride in 100 ml of anhydrous toluene. The reaction mixture is kept at 130° C. for two hours, then a solution of 16.5 g (0.11 moles) of 1-dimethylamino-3-chloro-2-methyl-propane in 20 ml of anhydrous toluene is added, and the mixture is allowed to stand at 130° C. for further 8 hours. The mixture is cooled and shaken with a solution of 16.5 g (0.11 moles) of tartaric acid in 80 ml of water. The aqueous phase is made alkaline to pH 10 with concentrated ammonium hydroxide at 0°–5° C. and extracted with dichloroethane. The organic phase is separated, dried over anhydrous magnesium sulfate and evaporated. The residual base can be used for salt formation without distillation.

Yield: 31 g (90%)
Hydrogen fumarate, m.p.: 140°–146° C.
Analysis for $C_{27}H_{41}NO_5$ (459.633):
Calculated: C: 70.55%, H: 8.99%, N: 3.04%,
Found: C: 71.02%, H: 8.90%, N: 3.01%.

EXAMPLE 3

Preparation of (±)-2-benzyl-2-(2'-diisopropylaminoethoxy)-1,7,7-trimethyl-bicyclo(2,2,1) heptane On starting from 3.9 g (0.1 mole) of sodium amide, 24.4 g (0.1 mole) of (±)-2-benzyl-1,7,7-trimethyl-bicyclo(2,2,1) heptan-2-ol and 18.0 g (0.11 moles) of 1-diisopropylamino-2-chloro-ethane, one proceeds in the way specified in Example 1.
Yield: 30 g (80.7%) of a pale yellow oil
B.p.: 190°–191° C./133.3 Pa
Hydrogen fumarate, m.p.: 128°–130° C.

$$K\left(\frac{octanol}{water}\right) = 1.15$$

Analysis for $C_{29}H_{45}NO_5$ (487.687):
Calculated: C: 71.42%, H: 9.3%, N: 2.87%,
Found: C: 71.9%, H: 9.33%, N: 2.89%.

EXAMPLE 4

Preparation of (±)-2-benzyl-2-[1'-(4''-benzylpiperazinyl)-propoxy]-1,7,7-trimethyl-bicyclo(2,2,1) heptane On starting from 3.9 g (0.1 mole) of sodium amide, 24.4 g (0.1 mole) of (±)-2-benzyl-1,7,7-trimethyl-bicyclo(2,2,1)heptan-2-ol and 27.8 g (0.11 mole) of 1-benzyl-4-(3'-chloro-propyl)-piperazine, one proceeds in the way specified in Example 2.
Yield: 38 g (82.6%) of a yellow viscous oil.
Dihydrogen fumarate, m.p.: 207°–209.55° C.
Analysis for $C_{39}H_{52}N_2O_9$ (692.861):
Calculated: C: 67.6%, H: 7.57%, N: 4.03%,
Found: C: 67.25%, H: 7.68%, N: 4.04%.

EXAMPLE 5

Preparation of (±)-2-benzyl-2-(3'-diisopropylaminopropoxy)-1,7,7-trimethyl-bicyclo(2,2,1)heptane On starting from 2.4 g (0.1 mole) of sodium hydride, 24.4 g (0.1 mole) of (±)-2-benzyl-1,7,7-trimethyl-bicyclo(2,2,1)heptan-2-ol and 19.55 g (0.11 moles) of 1-diisopropylamino-3-chloro-propane, one proceeds in the way as specified in Example 2.
Yield: 36.05 g (93.5%)
Hydrogen fumarate, m.p.: 93°–95° C.
Analysis for $C_{30}H_{47}NO_5$ (501.714):
Calculated: C: 71.82%, H: 9.44%, N: 2.79%,
Found: C: 71.50%, H: 9.61%, N: 2.69%.

EXAMPLE 6

Preparation of (±)-2-benzyl-2-(3'-diethylaminopropoxy)-1,7,7-trimethyl-bicyclo(2,2,1)heptane On starting from 2.4 g (0.1 mole) of sodium hydride, 24.4 g (0.1 mole) of (±)-2-benzyl-1,7,7-trimethyl-bicyclo(2,2,1)heptan-2-ol and 16.46 g (0.11 moles) of 1-diethylamino-3-chloro-propane, one proceeds in the way specified in Example 2.
Yield: 33 g (92.4%)
Hydrogen fumarate, m.p.: 123.5°–125.5° C.
Analysis for $C_{28}H_{43}NO_5$ (473.66):
Calculated: C: 71.00%, H: 9.15%, N: 2.96%,
Found: C: 71.40%, H: 9.06%, N: 2.98%.

EXAMPLE 7

Preparation of D-(−)-2-benzyl-2-(3'-dimethylaminopropoxy)-1,7,7-trimethyl-bicyclo(2,2,1)heptane On starting from 3.9 g (0.1 mole) of sodium amide, 24.4 g (0.1 mole) of D-(+)-2-benzyl-1,7,7-trimethyl-bicyclo(2,2,1)heptan-2-ol ($[\alpha]20_D^2 = +13.72°$; c=2, ethanol), and 13.4 g (0.11 moles) of 1-dimethylamino-3-chloro-propane, one proceeds in the way as specified in Example 1.
Yield: 30.87 g (93.7%) of a pale yellow oil
B.p.: 180°–186° C./133.3 Pa
$[\alpha]_D^{20} = -2.175°$ C. (c=2; ethanol)
Hydrogen fumarate, m.p.: 144°–146° C.

$$K\left(\frac{octanol}{water}\right) = 5.57$$

$[\alpha]_D^{20} = -1.66°$ (c=2; ethanol)
Analysis for $C_{26}H_{39}NO_5$ (445.606):
Calculated: C: 70.08%, H: 8.82%, N: 3.14%,
Found: C: 70.48%, H: 8.89%, N: 3.10%.

EXAMPLE 8

Preparation of D-(+)-2-benzyl-2-(2'-diethylaminoethoxy)-1,7,7-trimethyl-bicyclo(2,2,1)heptane On starting from 3.9 g (0.1 mole) of sodium amide, 24.4 g (0.1 mole) of D-(+)-2-benzyl-1,7,7-trimethyl-bicyclo(2,2,1)heptan-2-ol and 14.9 g (0.11 moles) of 1-diethylamino-2-chloro-ethane, one proceeds as specified in Example 1.
Yield: 29.9 g (87%) of a pale yellow oil
B.p.: 157°–163° C./53.3 Pa
$[\alpha]_D^{20} = +3.48°$ C. (c=2, ethanol)
Hydrogen fumarate, m.p.: 126.5°–130.5° C.
$[\alpha]_D^{20} = +2.6°$ C. (c=2, ethanol)
Analysis for $C_{27}H_{41}NO_5$ (459.633):
Calculated: C: 70.55%, H: 8.99%, N: 3.05%,
Found: C: 70.74%, H: 9.12%, N: 3.09%.

EXAMPLE 9

Preparation of (±)-2-benzyl-2-(3'-morpholino-propoxy)-1,7,7-trimethyl-bicyclo(2,2,1)heptane On starting from 24.4 g (0.1 mole) of (±)-2-benzyl-1,7,7-trimethyl-bicyclo(2,2,1)heptan-2-ol and 18.0 g (0.11 moles) of 1-chloro-3-morpholino-propane, one proceeds in the way as in Example 2.
Yield: 30.57 g (82.3%)
Hydrogen fumarate, m.p.: 76°–78° C.
Analysis for $C_{28}H_{41}NO_6$ (487.62):
Calculated: C: 68.96%, H: 8.48%, N: 2.87%,
Found: C: 68.26%, H: 8.4%, N: 2.84%.

EXAMPLE 10

Preparation of (±)-2-(3'-dimethylaminopropoxy)-2-(4''-methoxyphenyl)-1,7,7-trimethyl-bicyclo(2,2,1)heptane On starting from 3.9 g (0.1 mole) of sodium amide, 26.0 g (0.1 mole) of (±)-2-(4'-methoxyphenyl)-1,7,7-trimethyl-bicyclo(2,2,1)heptan-2-ol and 13.4 g (0.11 moles) of 1-dimethylamino-3-chloro-propane, one proceeds as in Example 2.
Yield: 26.8 g (77.5%)
Hydrogen fumarate, m.p.: 148°–149° C.
Analysis for $C_{26}H_{39}NO_6$ (461.606):
Calculated: C: 67.65%, H: 8.52%, N: 3.03%,
Found: C: 67.6%, H: 8.48%, N: 3.00%.

EXAMPLE 11

Preparation of
(±)-2-(p-chloro-benzyl)-2-(3'-dimethylaminopropoxy)-1,7,7-trimethyl-bicyclo(2,2,1)heptane On starting from 3.9 g (0.1 mole) of sodium amide, 27.9 g (0.1 mole) of (±)-2-(p-chloro-benzyl)-1,7,7-trimethyl-bicyclo(2,2,1)heptan-2-ol and 14.4 g (0.11 moles) of 1-dimethylamino-3-chloro-propane, one proceeds as in Example 1.

Yield: 32.5 g (89.3%) of a pale yellow, viscous oil
B.p.: 171°–173° C./46.7 Pa
Hydrogen fumarate, m.p.: 145°–146° C.

$$K\left(\frac{octanol}{water}\right) = 3.64$$

Analysis for $C_{26}H_{38}ClNO_5$ (480.06):
Calculated: C: 65.05%, H: 7.98%, Cl: 7.39%, N: 2.91%,
Found: C: 64.9%, H: 8.04%, Cl: 7.24%, N: 2.83%.

EXAMPLE 12

Preparation of
(±)-2-(p-chloro-benzyl)-2-(2'-dimethylaminoethoxy)-1,7,7-trimethyl-bicyclo(2,2,1)heptane On starting from 3.9 g (0.1 mole) of sodium amide, 27.9 g (0.1 mole) of (±)-2-(p-chloro-benzyl)-1,7,7-trimethyl-bicyclo(2,2,1)heptan-2-ol and 14.9 g (0.11 moles) of 1-diethylamino-2-chloro-ethane, one proceeds as specified in Example 1.

Yield: 35.4 g (93.7%) of a pale yellow viscous oil
B.p.: 162°–167° C./26.7 Pa
Hydrogen fumarate, m.p.: 110°–112° C.

$$K\left(\frac{octanol}{water}\right) = 5.64$$

Analysis for $C_{27}H_{40}ClNO_5$ (494.08):
Calculated: C: 65.64%, H: 8.16%, Cl: 7.17%, N: 2.83%,
Found: C: 65.12%, H: 8.31%, Cl: 7.08%, N: 2.77%.

EXAMPLE 13

Preparation of
(+)-2-[(3'-dimethylamino-2'-methyl)-propoxy]-2-(p-chloro-phenyl)-1,7,7-trimethyl-bicyclo(2,2,1)heptane On starting from 3.9 g (0.1 mole) of sodium amide, 26.5 g (0.1 mole) of (+)-2-(p-chloro-phenyl)-1,7,7-trimethyl-bicyclo(2,2,1)heptan-2-ol and 16.5 g (0.11 mole) of 1-dimethylamino-2-methyl-3-chloro-propane, one proceeds as specified in Example 1.

Yield: 32.3 g (88.7%) of a pale yellow oil
B.p.: 154°–158° C./26.7 Pa
Hydrogen fumarate, m.p.: 159.5°–162.5° C.

$$K\left(\frac{octanol}{water}\right) = 2.47$$

Analysis for $C_{26}H_{38}ClNO_5$ (480.06):
Calculated: C: 65.05%, H: 7.98%, Cl: 7.38%, N: 2.91%,
Found: C: 65.30%, H: 8.15%, Cl: 7.38%, N: 3.03%.

EXAMPLE 14

Preparation of
(±)-2-(3'-dimethylaminopropoxy)-2-phenyl-1,7,7-trimethyl-bicyclo(2,2,1)heptane On starting from 3.6 g (0.1 mole) of sodium amide, 23.04 g (0.1 mole) of (±)-2-phenyl-1,7,7-trimethyl-bicyclo(2,2,1)-heptan-2-ol and 13.4 g (0.11 moles) of 1-dimethylamino-3-chloropropane, one proceeds as specified in Example 1. Yield: 28.6 g (90.64%) of a pale yellow oil
B.p.: 157°–160° C./160 Pa,
Hydrogen fumarate, m.p.: 169.5°–171.5° C.,
Analysis for $C_{25}H_{37}NO_5$ (431.58):
Calculated: C: 69.58%, H: 8.64%, N: 3.24%,
Found: C: 69.65%, H: 8.36%, N: 3.18%.

EXAMPLE 15

Preparation of
(±)-2-(2'-dimethylaminoethoxy)-2-phenyl-1,7,7-trimethyl-bicyclo(2,2,1)heptane 3.9 g (0.1 g atom) of potassium metal are added to 100 ml of anhydrous xylene, and the mixture is reacted with 23.04 g (0.1 mole) of (±)-2-phenyl-1,7,7-trimethyl-bicyclo(2,2,1)heptan-2-ol under vigorous stirring. When the formation of hydrogen gas has ceased, a solution of 10.3 g (0.11 moles) of 1-dimethylamino-2-chloro-ethane in 30 ml of anhydrous xylene is introduced, under further stirring. The reaction mixture is kept at 100° C. for 6 hours, then washed thrice with 50 ml of water, and extracted with a solution of 15 g (0.1 mole) of tartaric acid in 80 ml of water or with 0.11 mole of diluted aqueous hydrochloric acid. The aqueous phase is made alkaline to pH 10 with an aqueous solution of potassium hydroxide of 20% under cooling (at 0°–5° C.). The base separated as an oil is extracted with ether. After distilling off the solvent the residue is either purified with fractionated distillation under vacuo or used for salt formation without any purification.

Yield: 25.2 g (83.6%) of a pale yellow oil,
B.p.: 131°–135° C./26.7 Pa,
Hydrogen fumarate, m.p.: 180°–182° C.
Analysis for $C_{24}H_{35}NO_5$ (417.55):
Calculated: C: 69.03%, H: 8.45%, N: 3.35%,
Found: C: 69.05%, H: 8.59%, N: 3.44%.

EXAMPLE 16

Preparation of
(±)-2-(3-diethylaminopropoxy)-2-phenyl-1,7,7-trimethyl-bicyclo(2,2,1)heptane On starting from 3.9 g (0.1 mole) of sodium amide, 23.04 g (0.1 mole) of (±)-2-phenyl-1,7,7-trimethyl-bicyclo(2,2,1)heptan-2-ol and 16.46 g (0.11 moles) of 1-diethylamino-3-chloro-propane one proceeds as specified in Example 1.

Yield: 23.5 g (68.4%)
Hydrogen fumarate, m.p.: 160°–163° C.
Analysis for $C_{27}H_{41}NO_5$ (459.63):
Calculated: C: 70.55%, H: 8.99%, N: 3.05%,
Found: C: 70.58%, H: 8.95%, N: 3.05%.

EXAMPLE 17

Preparation of
(±)-2-(2'-diethylaminoethoxy)-2-(2''-thienyl)-1,7,7-trimethyl-bicyclo(2,2,1)heptane On starting from 3.9 g (0.1 mole) of sodium amide, 23.6 g (0.1 mole) of (±)-2-(2'-thienyl)-1,7,7-trimethylbicyclo(2,2,1)heptan-2-ol and 14.9 g (0.11 mole) of 1-diethylamino-2-chloro-ethane one proceeds as specified in Example 2.

Yield: 27.4 g (81.7%)

Hydrogen fumarate, m.p.: 132.5°–135.5° C.

$$K\left(\frac{octanol}{water}\right) = 1.19$$

Analysis for $C_{24}H_{37}NO_5S$ (451.61):

Calculated: C: 63.83%, H: 8.25%, N: 3.10%, S: 7.10%,

Found: C: 64.10%, H: 8.27%, N: 3.15%, S: 7.05%.

EXAMPLE 18

Preparation of (±)-2-(3'-dimethylaminopropoxy)-2-(2''-thienyl)-1,7,7-trimethyl-bicyclo(2,2,1)heptane On starting from 3.9 g (0.1 mole) of sodium amide, 23.6 g (0.1 mole) of (±)-2-(2'-thienyl)-1,7,7-trimethyl-bicyclo(2,2,1)heptan-2-ol and 13.4 g (0.11 moles) of 1-dimethylamino-3-chloro-propane, one proceeds as specified in Example 2.

Yield: 30.7 g (95.6%)

Hydrogen fumarate, m.p.: 147°–149° C.

$$K\left(\frac{octanol}{water}\right) = 1.12$$

Analysis for $C_{23}H_{35}NO_5S$ (437.61):

Calculated: C: 63.13%, H: 8.06%, N: 3.20%, S: 7.32%,

Found: C: 63.45%, H: 8.20%, N: 3.14%, S: 7.36%.

EXAMPLE 19

Preparation of (±)-2-(3'-diethylaminopropoxy)-2-(2''-thienyl)-1,7,7-trimethyl-bicyclo(2,2,1)heptane On starting from 3.9 g (0.1 mole) of sodium amide, 23.6 g (0.1 mole) of (±)-2-(2'-thienyl)-1,7,7-trimethyl-bicyclo(2,2,1)heptan-2-ol and 16.46 g (0.11 moles) of 1-diethylamino-3-chloro-propane, one proceeds as specified in Example 2.

Yield: 32.4 g (96.6%),

Hydrogen fumarate, m.p.: 113°–115° C.,

Analysis for $C_{25}H_{33}NO_5S$ (465.66):

Calculated: C: 64.48%, H: 8.44%, N: 3.01%, S: 6.88%,

Found: C: 64.25%, H: 8.64%, N: 3.04%, S: 6.80%.

EXAMPLE 20

Preparation of (±)-2-dimethylaminoethoxy-2-phenyl-1,7,7-trimethyl-bicyclo(2,2,1)heptane Into a flask equipped with a stirrer and filled with nitrogen there are weighed 60 ml of anhydrous ether and 3.3 g of lithium metal cut in small pieces. After starting the stirrer 1–2 ml from 31.3 g (0.2 mole) of bromobenzene are added. The further amount of bromobenzene is diluted with 60 ml of anhydrous ether and added to the reaction mixture so that it should keep boiling. When the total amount of bromobenzene is added the mixture is kept boiling for an hour, then cooled to room temperature and the excess of lithium is filtered off. Thereafter the solution is reacted with a solution of 27.4 g (0.18 moles) of (±)-1,7,7-trimethyl-bicyclo(2,2,1)heptane in 50 ml of anhydrous ether under stirring, and the mixture is kept boiling for two hours. Then a solution of 18.54 g (0.198 moles) of 1-dimethylamino-2-chloro-ethane in 20 ml of anhydrous ether is added. After refluxing for a few hours the reaction is completed. The mixture is cooled to room temperature and washed several times with water until neutral. Then a solution of 20.88 g (0.18 mole) of fumaric acid in 200 ml of water is added, and the mixture is stirred for two hours. The crystals are filtered off and dried.

Yield: 68.9 g (91.7%) of (±)-2-dimethylaminoethoxy-2-phenyl-1,7,7-trimethyl-bicyclo(2,2,1)heptane hydrogen fumarate, M.p.: 180°–182° C., Analysis for $C_{24}H_{35}NO_5$ (417.55):

Calculated: C: 69.03%, H: 8.45%, N: 3.35%,

Found: C: 68.93%, H: 8.40%, N: 3.27%.

EXAMPLE 21

Preparation of (±)-2-benzyl-2-[3'-(N-cyclohexyl-N-methyl)aminopropoxy]-1,7,7-trimethyl-bicyclo(2,2,1)heptane On starting from 2.4 g (0.1 mole) of sodium hydride, 24.4 g (0.1 mole) of (±)-2-benzyl-1,7,7-trimethyl-bicyclo(2,2,1)heptane-2-ol, 41.5 g (0.11 moles) of 1-(N-cyclohexyl-N-methyl)amino-3-chloropropane, 140 ml of anhydrous toluene and 64 ml of anhydrous dimethylformamide, the reaction is effected at 80° C. as specified in Example 2.

Yield: 37.56 g (94.7%),

Hydrogen fumarate, m.p.: 186° C. (decomp.),

Analysis for $C_{31}H_{47}NO_5$ (513.73):

Calculated: C: 72.48%, H: 9.22%, N: 2.73%,

Found: C: 72.50%, H: 9.31%, N: 2.70%.

EXAMPLE 22

Preparation of (±)-2-(p-methoxyphenyl)-2-(3'-dimethylaminopropoxy)-1,7,7-trimethyl-bicyclo(2,2,1)heptane a. 4.8 g (0.2 g atom) of granulated magnesium metal are added to a solution of 37.4 g (0.2 moles) of 4-bromoanisole. The Grignard-reagent thus-obtained is reacted with a solution of 30 g (0.2 moles) of (±)-1,7,7-trimethyl-bicyclo(2,2,1)heptan-2-one in 20 ml of anhydrous ether. After refluxing for a few hours the Grignard complex is decomposed with a solution of 24 g of ammonium chloride in 80 ml of ice-cold water. The ether phase is separated, dried over magnesium sulfate and made free of solvent in vacuo. The residue of the evaporation is purified by fractionated distillation in vacuo. Yield: 43.9 g (84.4%) of a colourless viscous oil B.p.: 155°–165° C./173 Pa b. On starting from a 50% suspension of 7.8 g (0.1 mole) of sodium amide in benzene, 26.03 g (0.1 mole) of (±)-2-(p-methoxyphenyl)-1,7,7-trimethyl-bicyclo(2,2,1-)heptan-2-ol and 13.4 g (0.11 moles) of 1-dimethylamino-3-chloropropane, one proceeds as specified in Example 1.

Yield: 29.7 g (85.96%) of a pale yellow viscous oil,

Hydrogen fumarate, m.p.: 149°–151° C.,

Analysis for $C_{26}H_{39}NO_6$ (461.6):

Calculated: C: 67.65%, H: 8.52%, N: 3.03%,

Found: C: 68.01%, H: 8.61%, N: 3.11%.

EXAMPLE 23

Tablets containing 25 mg of
(±)-2-benzyl-2-(3'-diethylaminopropoxy)-1,7,7-trimethyl-bicyclo(2,2,1)heptane hydrogen fumarate The composition of a tablet is as follows:

| Active ingredient: | 25.0 mg |
|---|---|
| Maize starch: | 97.0 mg |
| Polivinyl pyrrolidone: | 175.0 mg |
| Magnesium stearate: | 3.0 mg |
| | 300.0 mg |

A mixture of the active ingredient and the maize starch is moistened with 10–15% aqueous polivinyl pyrrolidone, then granulated and dried at 40°–45° C. After repeated drying the granulate is mixed with the magnesium stearate and pressed into tablets weighing 300 mg.

EXAMPLE 24

Dragées containing 25 mg of
(±)-2-benzyl-2-[3'-(dimethylamino)-2'-methyl-propoxy]-1,7,7-trimethyl-bicyclo(2,2,1)heptane hydrogen fumarate The composition of a dragée kernel is as follows:

| Active ingredient: | 25.0 mg |
|---|---|
| Maize starch: | 245.0 mg |
| Gelatine: | 8.0 mg |
| Talc: | 18.0 mg |
| Magnesium stearate: | 4.0 mg |
| | 300.0 mg |

A mixture of the active ingredient and the maize starch is moistened with a 10% aqueous gelatine solution, then granulated by passing through a sieve and dried at 40°–45° C. The dry granulate is repeatedly sieved, homogenized with the talc and the magnesium stearate, finally compressed to dragée kernels of 300 mg each.

EXAMPLE 25

Dragées containing 50 mg of
D-(+)-2-benzyl-2-(2'-diethylaminoethoxy)-1,7,7-trimethyl-bicyclo(2,2,1)heptane hydrogen fumarate The composition of a dragée kernel is as follows:

| Active ingredient: | 50.0 mg |
|---|---|
| Lactose: | 97.0 mg |
| Polivinyl pyrrolidone | 2.0 mg |
| Magnesium stearate | 1.0 mg |
| | 150.0 mg |

The granulate is prepared as in the foregoing Example. The weight of a dragée kernel is equal to 150 mg. The dragée kernels are coated in a manner known per se, by a layer consisting of sugar and talc. The finished dragée is coloured with a suitable non-toxic food pigment and polished with beewax.

EXAMPLE 26

Gelatine capsules containing 25 mg of active ingredient

The composition of a gelatine capsule is as follows:

| Active ingredient: | 25.0 mg |
|---|---|
| Maize starch: | 265.0 mg |
| Aerosil: | 6.0 mg |
| Magnesium stearate: | 4.0 mg |
| | 300.0 mg |

The components are homogenized and then filled into gelatine capsules of an adequate size.

EXAMPLE 27

Injectable solution containing 25 mg of active substance

An ampoule contains 25.0 mg of the active ingredient in 5 ml of twice distilled water.

What we claim is:

1. A basic ether of the formula (I) or a pharmaceutically acceptable acid addition salt or quaternary salt hereof

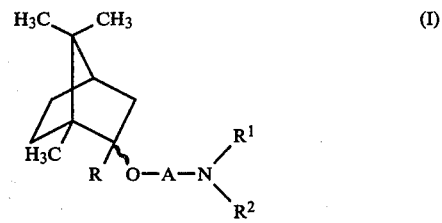

wherein
   $R^1$ and $R^2$ are the same or different and each can represent a $C_{1-5}$ alkyl group or a $C_{3-6}$ cycloalkyl group or they form together with the adjacent nitrogen atom, a piperidino, pyrrolidino, morpholino, thiomorpholino, piperazino, N-$C_{1-3}$ alkyl-piperazino, N-phenyl-piperazino or N-benzyl-piperazino group,
   R is phenyl, phenyl-($C_{1-3}$ alkyl) or thienyl which can be substituted by one or more halogen or $C_{1-3}$ alkoxy substituents,
   A is $C_{2-5}$ straight or branched alkylene chain, and ⇌ represents a valence bond of α or β configuration.

2. The compound defined in claim 1, wherein $R^1$ and $R^2$ are each methyl or ethyl, R is phenyl, benzyl or $C_{1-3}$-alkoxy-phenyl group which can be substituted by $C_{1-3}$ alkoxy, and A is ethylene, propylene or 2-methyl-propylene.

3. 2-Benzyl-2-(3'-dimethylamino-2'-methyl-propoxy)-1,7,7-trimethyl-bicyclo(2,2,1)heptane or a pharmaceutically acceptable acid addition salt thereof as defined in claim 1.

4. 2-Benzyl-2-(3'-diethylaminopropoxy)-1,7,7-trimethyl-bicyclo(2,2,1)heptane or a pharmaceutically acceptable acid addition salt thereof as defined in claim 1.

5. 2-Benzyl-2-(2'-diethylaminoethoxy)-1,7,7-trimethyl-bicyclo(2,2,1)heptane or a pharmaceutically acceptable acid addition salt thereof as defined in claim 1.

6. A compound as defined in claim 1 and selected from the group consisting of 2-Phenyl-2-(3'-dimethylaminopropoxy)-1,7,7-trimethyl-bicyclo(2,2,1)heptane,
   2-phenyl-2-(2'-dimethylaminoethoxy)-1,7,7-trimethyl-bicyclo(2,2,1)heptane,
   2-phenyl-2-(3'-diethylaminopropoxy)-1,7,7-trimethyl-bicyclo(2,2,1)heptane, or 2-(p-methoxyphenyl)-2-(3'-dimethylaminopropoxy)-1,7,7-trimethyl-bicyclo(2,2,1)heptane,
and pharmaceutically acceptable acid addition salts thereof.

7. A pharmaceutical composition possessing tranquilizing, analgesic, antiparkinsonism and antiepileptic effect, comprising an effective amount of a compound as defined in claim 1 or a pharmaceutically effective salt thereof, together with an appropriate inert, non-toxic solid or liquid pharmaceutical carrier.

8. An analgesic, tranquilizing antiparkinsonism or antiepileptic method of treatment comprising administering to an animal subject an effective amount of a compound as defined in claim 1 or a pharmaceutically effective salt thereof.

* * * * *